United States Patent [19]
Donovan

[11] Patent Number: 5,766,248
[45] Date of Patent: Jun. 16, 1998

[54] METHOD AND APPARATUS FOR FORMING A TISSUE POCKET TO RECEIVE AN IMPLANTABLE DEVICE

[75] Inventor: Maura G. Donovan, St. Paul, Minn.

[73] Assignee: Medtronic, Inc., Minneapolis, Minn.

[21] Appl. No.: 637,459

[22] Filed: Apr. 25, 1996

[51] Int. Cl.$^6$ .............................. A41D 19/00; A61F 2/02
[52] U.S. Cl. .................. 623/11; 2/161.7; 2/167; 2/21
[58] Field of Search .................. 623/11; 2/21, 161.7, 2/167

[56] References Cited

U.S. PATENT DOCUMENTS

| | | | |
|---|---|---|---|
| 1,999,753 | 4/1935 | Diemer | 2/167 |
| 2,461,970 | 2/1949 | Finegan | 2/21 |
| 3,342,182 | 9/1967 | Charos | 2/161.7 |
| 5,344,455 | 9/1994 | Keogh et al. | 623/11 |
| 5,476,509 | 12/1995 | Keogh et al. | 623/1 |

OTHER PUBLICATIONS

Brochure entitled "Fibracol® Collagen-Alginate Wound Dressing", Johnson & Johnson Medical, Inc., 2 pgs (1995).
A. Fisher, "Science Newsfront", *Popular Science* (1989).
D.L. Mooradian et al., "Effect of Glow Discharge Surface Modification of Plasma TFE Vascular Graft Material on Fibronectin and Laminin Retention and Endothelial Cell Adhesion", *J. Surg. Res.*, 53, 74–81 (1992).
Brochure entitled "Step Up to ... a New Age in Wet Wound Management", 2 pgs (undated).

*Primary Examiner*—Randy C. Shay
*Attorney, Agent, or Firm*—Thomas F. Woods; Harold R. Patton

[57] ABSTRACT

A dissection glove for forming in a patient a tissue pocket to receive an implantable device. The dissection glove is constructed of an absorbent material formed into at least one recess with an open end for receiving a portion of a surgeon's gloved hand. A retaining mechanism is provided for releasably retaining the dissection glove to a portion of the surgeon's gloved hand. An extraction mechanism is optionally provided for extracting the dissection glove from the tissue pocket. The dissection glove may be constructed from a variety of materials, such as polypropylene nonwoven mesh or calcium alginate gauze. The present invention is also directed to a method of forming a tissue pocket in a patient for receiving an implantable device using the present dissection glove.

11 Claims, 2 Drawing Sheets

METHOD AND APPARATUS FOR FORMING A TISSUE POCKET TO RECEIVE AN IMPLANTABLE DEVICE

FIELD OF THE INVENTION

The present invention is directed to a method and apparatus for forming a tissue pocket to receive an implantable device, and more particularly, to the use of a dissection glove to aid in the formation of a tissue pocket for an implantable device.

BACKGROUND OF THE INVENTION

Currently, surgeons use their gloved fingers to perform a blunt dissection to form a tissue pocket for receiving an implantable device. After the tissue pocket is formed, the surgeon typically packs the tissue pocket with gauze to help achieve hemostasis prior to inserting the implantable device. It is also common to irrigate the tissue pocket with an antimicrobial solution. After hemostasis is achieved, the gauze is removed from the tissue pocket and the implantable device is inserted.

Friction caused by the rough texture of the surgeons gloves tends to traumatize the tissue surrounding the tissue pocket. Conventional gauze used to achieve hemostasis tends to adhere to the tissue surrounding the tissue pocket. Consequently, hemostasis can be compromised by removing the gauze from the tissue pocket prior to insertion of the implantable device. Finally, the current three-step process is time consuming during the critical implantation phase.

SUMMARY OF THE INVENTION

The present invention is directed to a dissection glove for forming a tissue pocket to receive an implantable device.

The dissection glove of the present invention is constructed of an absorbent material formed to have at least one recess with an open end for receiving a portion of a surgeon's gloved hand. A retaining mechanism is provided for releasably retaining the dissection glove to the surgeon's gloved hand. An extraction mechanism is provided for extracting the dissection glove from the tissue pocket.

The dissection glove may be constructed from a variety of materials, such as polypropylene nonwoven mesh or calcium alginate gauze. In one embodiment, the absorbent material comprises a glow-discharge treated material coated with an antimicrobial material.

In one embodiment, the at least one recess in the dissection glove is formed to receive an index and a middle finger of the surgeon's gloved hand. In an alternate embodiment, the at least one recess includes a pair of adjacent recesses to permit independent articulation of adjacent fingers of the surgeon's gloved hand. In yet another embodiment, the at least one recess corresponds to the shape of the implantable device, such as circular, rectangular or a variety of other shapes.

The retaining mechanism is preferably elastic extending around a perimeter of the open end. The extraction mechanism is preferably a retrieval loop attached to the dissection glove proximate to the open end.

The present method for forming a tissue pocket in a patient for receiving an implantable device includes positioning a dissection glove over a portion of a surgeon's gloved hand. The engaging mechanism retains the dissection glove to the portion of the surgeon's hand. A blunt dissection is performed to form the tissue pocket using the portion of the surgeon's hand covered by the dissection glove. The portion of the surgeon's gloved hand is removed from the dissection glove so that the dissection glove remains in the tissue pocket. The dissection glove is subsequently removed from the tissue pocket prior to insertion of the implantable device.

The present method optionally includes irrigating the tissue pocket and dissection glove with a saline solution prior to extracting the dissection glove from the tissue pocket. At least partial hemostasis is preferably achieved prior to extracting the dissection glove from the tissue pocket. The step of removing the dissection glove from the tissue pocket may include gripping an extraction means on the dissection glove. The dissection glove is preferably substantially spread-out within the tissue pocket.

As used in this application:

Tissue pocket refers to an internal region of a patient that has been cut, deformed and/or stretched to receive an implantable device.

Implantable device refers to any medical device that is surgically placed in a patient's body, such as a drug pump, pacemaker device, implantable defibrillator or implantable pulse generators.

DETAILED DESCRIPTION OF THE PREFERRED EMBODIMENTS

Figure 1:
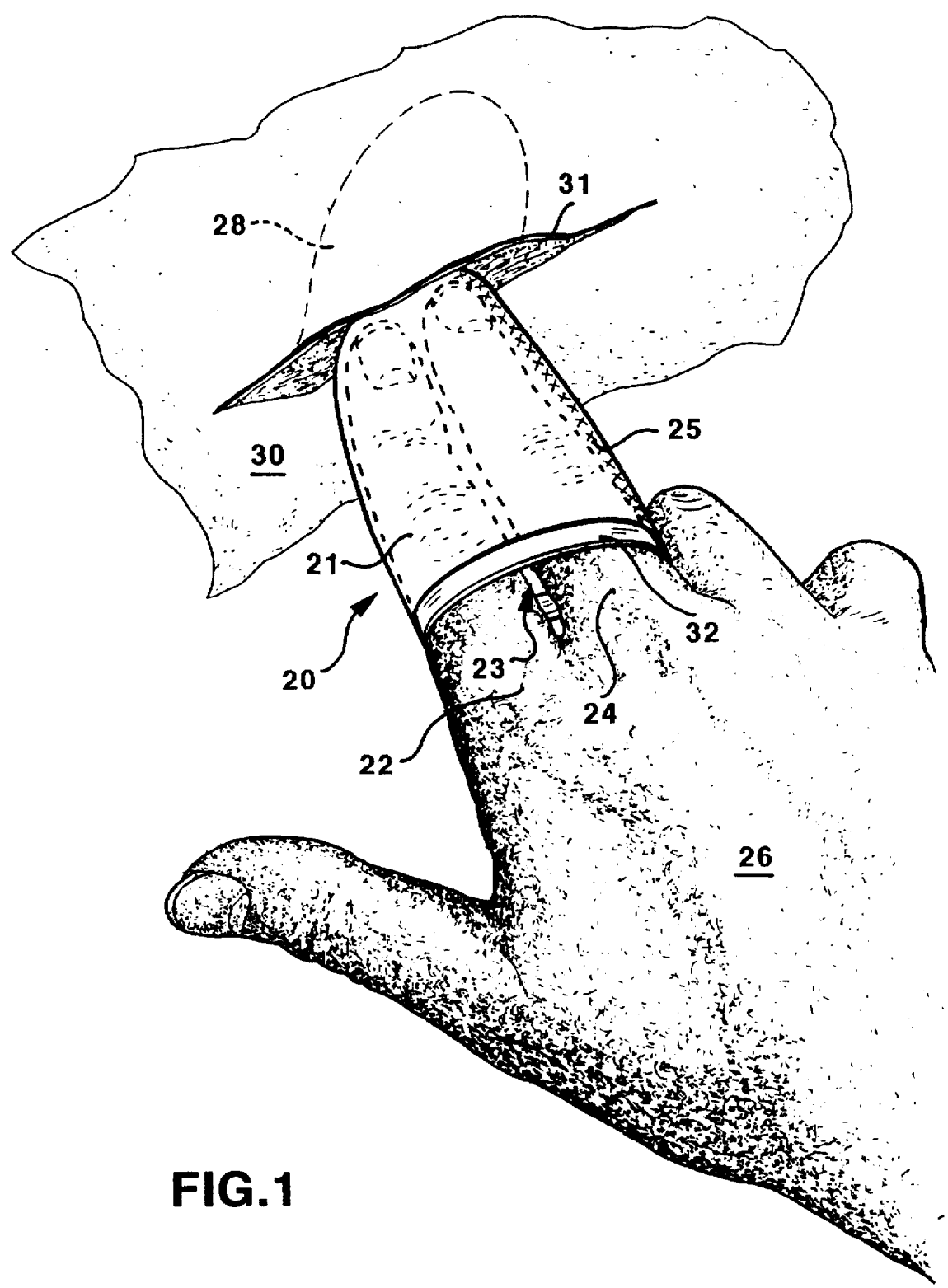
FIG. 1 illustrates the use of a dissection glove to form a tissue pocket in a patient.

FIG. 1 illustrates a dissection glove 20 forming a recess 21 with an open end 23 that is preferably sized to fit over the index finger 22 and middle finger 24 of the surgeon's gloved hand 26. It will be understood that the size of the dissection glove 20 may vary without departing from the scope of the present invention. For example, the dissection glove 20 may be enlarged to cover three or more fingers or other portions of the surgeon's hand 26. An elastic portion 32 retains the dissection glove 20 to the surgeon's fingers 22, 24. The surgeon performs a blunt dissection through an incision 31 using her index and middle fingers 22, 24 to form a tissue pocket 28 in the patient 30. It will be understood that the pleats or folds may be included to increase the surface area and absorbent capacity of the dissection glove 20.

As will be discussed below, the dissection glove 20 may be constructed from a material with enhanced lubricity. Alternatively, the surgeon may pre-wet the dissection glove 20 prior to forming the tissue pocket 28. The wetting solution may be saline or saline with an antimicrobial.

The choice of material for fabricating the dissection glove 20 is dictated by the need for tissue compatibility. The material must maintain its strength after fluid absorption and must be more absorbent than conventional gauze. Conventional gauze is typically constructed from specially woven or ravel resistant cotton.

The dissection glove 20 may be constructed from a variety of materials, such as collagen, a thermoplastic polymeric material, including melt-blown polymer fibers, such as melt-blown polypropylene fibers, and including spunbond polymer fiber such as spunbond polyethylene and polypropylene fibers, and synthetic polymer fibers, such as polypropylene, polyethylene or other polyolefins, polyester, acrylic, polyamide and nylon fibers; cellulose non-woven fibers such as rayon; and combinations of these materials. Commercially available materials suitable for use in constructing the present dissection glove 20 include a non-adhering packing strip sold under the tradename ADAPTIC from Johnson & Johnson located in Arlington, Tex.; Vaseline® petrolatum gauze available from Sherwood Medical located in St. Louis, Mo.; a sterile sodium chloride impregnated gauze dressing sold under the tradename Mesalt® and a non-adhering dressing sold under the tradename ETE® both from Scott Health Care of Bowling Green, Ky.; a 100% thermally bonded polyethylene with a density of 20 g/m$^2$ available under the trade designation 5220 and a 100% thermally bonded polypropylene with a density of 20 g/m$^2$ available under the trade designation 1520, both from Freudenberg Microfiber of Weinheim, Germany.

Alternatively, the absorbent material may be calcium alginate. Calcium alginate is known to have enhanced hemostatic properties and is more absorbent than conventional gauze. Calcium alginate transforms into a conformable, protective hydrogel when in contact with sodium-rich wound exudate. An alginic acid, calcium alginate is a polysaccharide and is insoluble in aqueous solutions. As the alginate is soluble in solutions containing sodium ions, it is easily removed by irrigation with a sterile solution of 0.9% saline or 1% sodium citrate, causing minimal damage to hemostasis. Calcium alginate fibers left behind in the tissue pocket 28 will biodegrade. It will be understood that laminates of one or more of these materials may be desirable for some applications.

Polypropylene or polyethylene nonwoven mesh may be surface treated to enhance its hydrophilic properties and to provide a surface that is suitable for ionic attachment of antimicrobial. The surface characteristics of the absorbent material used to construct the dissection glove 20 may be glow-discharge treated. Glow discharge treatment involves exposing the material to a plasma or ionized gas. Glow discharge in the presence of oxygen ($O_2$) results in a negative charge on the surface of the material. Glow discharge in the presence of ammonia ($NH_3$) results in a negative charge on the surface of the material. For example, polymyxin may be covalently attached to these polymers using carbodiimide attachment chemistry. Polymyxins may also be coupled ionically as a result of their cationic nature. Gentamicin is an aminoglycoside that may be covalently attached to these polymers. Further discussion of bioactive surfaces is set forth in U.S. Pat. Nos. 5,476,509 and 5,344,455, both of which are hereby incorporated by reference.

The dissection gloves in any of the embodiments disclosed herein may constructed by a variety of techniques. In the embodiment shown in FIG. 1, a sheet of absorbent material is folded and a seam 25 is formed along overlapping edges thereof. The seam 25 may be formed by a variety of techniques, including glues, adhesives, hot-melt adhesives, pressure sensitive adhesives, staples, mechanical fasteners, mating surface fasteners, or conventional sewing. In embodiments in which the absorbent material has a thermoplastic component, such as a polyolefin, polyester, polyetherester or polyamide, the seam 25 may be formed by thermal bonding or ultrasonic welding.

After the tissue pocket 28 is formed, the surgeon preferably slips the dissection glove 20 off of her fingers 22, 24 and leaves it behind in the tissue pocket 28 for a period of time to achieve hemostasis, as is known in the art. The period of time required to achieve hemostasis is a function of the type of tissue in which the tissue pocket 28 is formed, the size of the tissue pocket 28, and a variety of other factors. The period of time to achieve hemostasis should be about the same or less than using conventional techniques.

Prior to implantation of the implantable device, the surgeon removes the dissection glove 20 from the tissue pocket 28. A loop 34 (see FIG. 2) attached to the dissection glove 20 proximate the elastic portion 32 is optionally provided for gripping by the surgeon. The surgeon preferably irrigates the tissue pocket 28 with a saline solution prior to removal of the dissection glove 20. A dissection glove 20 constructed from calcium alginate is particularly easy to remove from the tissue pocket 28 because of the exchange of the insoluble calcium salt to the readily soluble sodium alginate.

Figure 2:
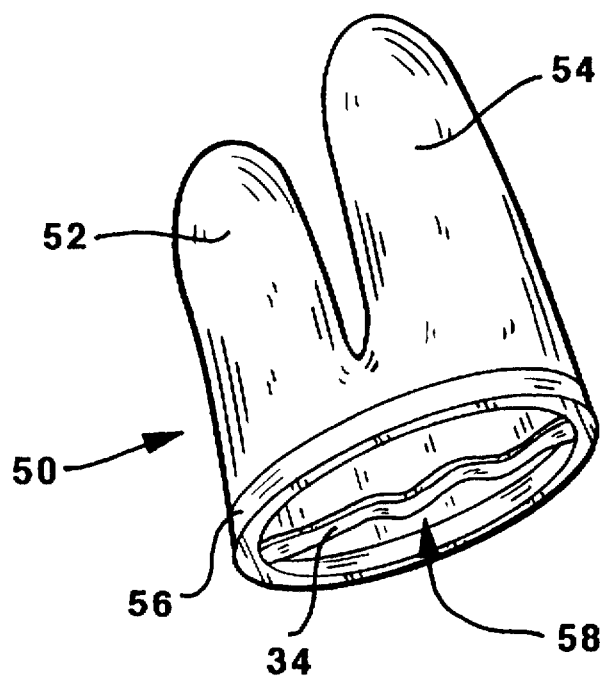
FIG. 2 illustrates an alternate shape of a dissection glove to permit independent articulation of adjacent fingers.

FIG. 2 illustrates an alternate dissection glove 50 formed with two finger receiving recesses 52, 54 to permit independent articulation of adjacent fingers on the surgeon's gloved hand. Elastic 56 is provided around the perimeter of the opening 58 to retain the dissection glove 50 on the surgeon's gloved fingers. The additional surface area of the dissection glove 50 has the added benefit of increased absorbency.

Figure 3:
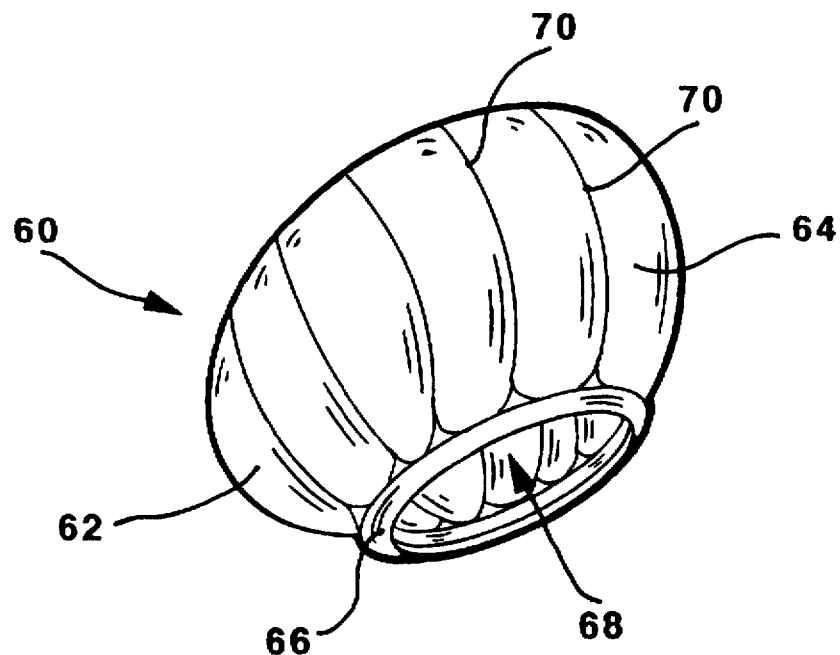
FIG. 3 illustrates a circular dissection glove corresponding to the shape of some implantable devices.

FIG. 3 is an alternate circular dissection glove 60 shaped to correspond to the circular shape of some implantable devices (not shown). Elastic 66 is provided around the perimeter of the opening 68. A series of pleats, folds or corrugations 70 may optionally be included to increase the surface area and the absorbent capacity of the of the glove 60. The surgeon's gloved fingers are permitted to move freely within the circular dissection glove 60 to form the tissue pocket into the desired circular shape. Edges 62, 64 of the dissection glove 60 may be arranged to conform to the contours of the tissue pocket so that the absorbent material extends substantially across the interior surface thereof. The absorbent material in the pleats 70 may also be used to conform the dissection glove 60 to the shape of the tissue pocket.

The present invention has now been described with reference to several embodiments described herein. It will be apparent to those skilled in the art that many changes can be made in the embodiments without departing from the scope of the invention. Thus, the scope of the present invention should not be limited to the structures described herein, but only to structures described by the language of the claims and the equivalents to those structures.

What is claimed is:

1. A sterile medical dissection glove for forming in a patient a tissue pocket to receive an implantable device, the dissection glove comprising an absorbent material forming at least one recess having an open end for receiving at least two fingers of a surgeon's gloved hand, elastic retaining means disposed propinquant to the open end for releasably retaining the dissection glove to the surgeon's gloved hand and retrieval loop extraction means for extracting the dissection glove from the tissue pocket.

2. The article of claim 1 wherein the absorbent material comprises polypropylene nonwoven mesh.

3. The article of claim 1 wherein the absorbent material comprises calcium alginate gauze.

4. The article of claim 1 wherein the at least one recess is formed to receive an index and a middle finger of the surgeon's gloved hand.

5. The article of claim 1 wherein the at least one recess comprises a pair of adjacent recesses for permitting independent articulation of adjacent fingers of the surgeon's gloved hand.

6. The article of claim 1 wherein the at least one recess comprises a circular shape.

7. The article of claim 1 further including a plurality of folds in the absorbent material to increase the surface area of the dissection glove.

8. The article of claim 1 wherein the retaining means comprises elastic extending around a perimeter of the open end.

9. The article of claim 1 wherein the extraction means comprises a retrieval loop attached to the dissection glove proximate the open end.

10. The article of claim 1 wherein the absorbent material comprises a glow-discharge treated material.

11. The article of claim 1 wherein the absorbent material comprises an antimicrobial material.

* * * * *